(12) United States Patent
Kim et al.

(10) Patent No.: US 11,746,072 B2
(45) Date of Patent: *Sep. 5, 2023

(54) METHOD OF REFINING RAFFINATE-2

(71) Applicant: LG CHEM, LTD., Seoul (KR)

(72) Inventors: Sung Kyun Kim, Daejeon (KR); Sung Kyu Lee, Daejeon (KR); Yong Mann Beyun, Daejeon (KR); Joon Ho Shin, Daejeon (KR); Ji Hye Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 450 days.

This patent is subject to a terminal disclaimer.

(21) Appl. No.: 16/625,333

(22) PCT Filed: Jul. 20, 2018

(86) PCT No.: PCT/KR2018/008223
§ 371 (c)(1),
(2) Date: Dec. 20, 2019

(87) PCT Pub. No.: WO2019/027165
PCT Pub. Date: Feb. 7, 2019

(65) Prior Publication Data
US 2021/0363075 A1  Nov. 25, 2021

(30) Foreign Application Priority Data
Jul. 31, 2017  (KR) .................. 10-2017-0096789

(51) Int. Cl.
*C07C 7/04* (2006.01)
*B01D 3/14* (2006.01)
(Continued)

(52) U.S. Cl.
CPC .............. *C07C 7/04* (2013.01); *B01D 3/007* (2013.01); *B01D 3/143* (2013.01); *B01D 3/146* (2013.01);
(Continued)

(58) Field of Classification Search
CPC .... C07C 7/04; C07C 7/05; C07C 7/06; C07C 7/08; B01D 3/007; B01D 3/322
See application file for complete search history.

(56) References Cited

U.S. PATENT DOCUMENTS

| 3,639,497 A | 2/1972 | Martel et al. |
| 4,515,661 A | 5/1985 | Ogure et al. |

(Continued)

FOREIGN PATENT DOCUMENTS

| CN | 101074183 A | 11/2007 |
| CN | 101605873 A | 12/2009 |

(Continued)

OTHER PUBLICATIONS

English translation of JP 2005-343898 obtained from Espacenet.*
(Continued)

*Primary Examiner* — Jonathan Luke Pilcher
(74) *Attorney, Agent, or Firm* — Bryan Cave Leighton Paisner LLP

(57) ABSTRACT

A method for separating and refining 1-butene with a high purity and a high yield from a raffinate-2 stream. The method includes: feeding raffinate-2 to a first distillation column; obtaining heavy raffinate-3 from a lower part of the first distillation column; recovering an upper part fraction containing 1-butene from an upper part of the first distillation column; feeding the upper part fraction containing 1-butene to a second distillation column; recovering a first lower part fraction rich in 1-butene from a lower part of the second distillation column and light raffinate-3 from an upper part
(Continued)

of the second distillation column. Heat of the upper part fraction recovered from the upper part of the first distillation column is fed to the lower part of the second distillation column through a first heat exchanger. Thus, 1-butene is obtained with high purity and high yield while maximizing an energy recovery amount by double-effect distillation.

7 Claims, 3 Drawing Sheets

(51) Int. Cl.
    *C07C 7/00* (2006.01)
    *B01D 3/00* (2006.01)
    *C07C 9/10* (2006.01)
    *C07C 11/08* (2006.01)

(52) U.S. Cl.
    CPC ............... *C07C 7/005* (2013.01); *C07C 9/10* (2013.01); *C07C 11/08* (2013.01)

(56) References Cited

U.S. PATENT DOCUMENTS

| | | | |
|---|---|---|---|
| 7,528,290 B2 * | 5/2009 | Zimmermann | B01D 1/007 202/152 |
| 10,793,788 B2 * | 10/2020 | Gomez | C10G 7/12 |
| 11,040,929 B2 * | 6/2021 | Kim | C10G 70/041 |
| 11,065,556 B2 * | 7/2021 | Kim | B01D 3/00 |
| 2008/0161618 A1 | 7/2008 | Zimmermann et al. | |
| 2010/0197987 A1 | 8/2010 | Almering | |
| 2011/0130604 A1 * | 6/2011 | Gartside | C07C 6/04 585/324 |
| 2016/0082363 A1 | 3/2016 | Lee et al. | |
| 2017/0166497 A1 | 6/2017 | Kim et al. | |
| 2019/0264115 A1 * | 8/2019 | Gomez | B01D 3/4283 |

FOREIGN PATENT DOCUMENTS

| | | |
|---|---|---|
| CN | 101792363 A | 8/2010 |
| CN | 102942475 A | 2/2013 |
| CN | 104829436 A | 8/2015 |
| CN | 104926587 A | 9/2015 |
| CN | 105229119 A | 1/2016 |
| CN | 106536459 A | 3/2017 |
| DE | 10 2005 062 700 A1 | 7/2007 |
| EP | 1 803 699 A2 | 7/2007 |
| JP | 55-81848 A | 6/1980 |
| JP | 58-92625 A | 6/1983 |
| JP | 2005-528415 A | 9/2005 |
| JP | 4307373 A | 9/2005 |
| JP | 2005-343898 A | 12/2005 |
| JP | 2012-516846 A | 7/2012 |
| JP | 2015-100724 A | 6/2015 |
| JP | 2016-525448 A | 8/2016 |
| KR | 2005-0025644 A | 3/2005 |
| KR | 2005-0089329 A | 8/2005 |
| KR | 2006-0120486 A | 11/2006 |
| KR | 2007-0070093 A | 7/2007 |
| KR | 2016-0107736 A | 9/2016 |
| KR | 2017-0084359 A | 7/2017 |

OTHER PUBLICATIONS

"Tower Packing Products and Technology Manual", Xu Chongsi, China National Chemical Equipment Corporation, Shanghai University of Engineering and Technology, Chemical Industry Press, Beijing, May 1995, p. 460 and English translation thereof.

European Opposition Report of European Patent Office in Appl'n No. 18840963.5, dated Nov. 23, 2022.

Myungwan Han et al., "Multivariable control of double-effect distillation configurations", J. Proc. Cont., vol. 6, No. 4, pp. 247-253, 1996.

* cited by examiner

METHOD OF REFINING RAFFINATE-2

CROSS-REFERENCE TO RELATED APPLICATIONS

This application is the U.S. national stage of international Application No. PCT/KR2018/008223, filed Jul. 20, 2018, and claims priority from Korean Application No. 10-2017-0096789, filed Jul. 31, 2017, the contents of which are incorporated by reference as if fully set forth herein.

TECHNICAL FIELD

The present invention relates to a method of refining a raffinate-2 stream discharged from a process of separating a C4 mixture, and more specifically, to a method of separating and refining 1-butene with a high purity and a high yield from a raffinate-2 stream.

BACKGROUND ART

A C4-fraction from the naphtha cracking center (raw C4) is a mixture of C4 materials with a single bond, a double bond, or a triple bond, which is also referred to as a C4 mixture (mixed C4).

Generally, a subsequent process from the C4-fraction involves a process of separating and removing butadiene, which is a raw material for the synthetic rubber. The butadiene is separated and removed by, for example, extraction or extractive distillation. A C4 stream that remains after removing the butadiene is a hydrocarbon mixture (corresponding to raffinate-1 or hydrocracking-C4) containing saturated hydrocarbons (n-butane and isobutane) together with the olefin (isobutene, 1-butene, and 2-butene). A method of removing isobutene from the mixture is to react isobutene with methanol to form methyl tertiary butyl ether (MTBE). The C4 mixture obtained after removing the butadiene and isobutene is referred to as raffinate-2 (see FIG. 1). 1-butene separated from raffinate-2 is useful as a raw material for linear low density polyethylene (LLDPE). The C4 remaining after separating 1-butene from the raffinate-2 is referred to as raffinate-3, and the raffinate-3 has trans-2-butene, cis-2-butene, and n-butane, and the like, as main components.

Components of the C4 mixture have small differences in boiling points and low separating factors, and thus it is difficult and uneconomical to perform distillation subsequent treatment that separates desired components in each step. In particular, it is not easy to separate 1-butene, which is separated from the raffinate-2, from a refinement process since 1-butene has almost the same boiling point as isobutene. The boiling point of isobutene is −6.9□ and the boiling point of 1-butene is −6.24□. In particular, when a ratio of isobutene/1-butene in a feed is high, it is difficult to design the refinement process, and in severe cases, there is a problem in that it is not possible to manufacture products. Therefore, it is necessary to develop a process capable of efficiently separating 1-butene with a high purity from the raffinate-2.

SUMMARY

An object of the present invention is to provide an energy-saving process capable of recovering 1-butene with a high purity and a high yield from a raffinate-2 stream.

In one general aspect, a method of refining raffinate-2 includes:

feeding a raffinate-2 containing n-butane, isobutane and 1-butene to a first distillation column to obtain heavy raffinate-3 containing n-butane from a lower part of the first distillation column and to recover an upper part fraction containing 1-butene from an upper part of the first distillation column; and feeding the upper part fraction containing 1-butene to a second distillation column to recover a first lower part fraction rich in 1-butene from a lower part of the second distillation column and to recover light raffinate-3 containing isobutane from an upper part of the second distillation column, wherein heat of the upper part fraction recovered from the upper part of the first distillation column is fed to the lower part of the second distillation column through a first heat exchanger.

The raffinate-2 fed to the first distillation column may contain isobutene and 1-butene at a weight ratio (isobutene/1-butene) of 0.006 or less.

An operating pressure of the second distillation column may be 4.7 kgf/cm$^2$ or more.

An operating pressure of the first distillation column may be higher than an operating pressure of the second distillation column by 3.5 kgf/cm$^2$ or more.

The upper part fraction of the first distillation column may be fed with heat to a second lower part fraction recovered from the lower part of the second distillation column through the first heat exchanger, a portion of the upper part fraction of the first distillation column may be fed with a feed stream to the second distillation column, and the remainder may be refluxed to the upper part of the first distillation column.

The second lower part fraction of the second distillation column that is fed with heat through the first heat exchanger may be refluxed to the second distillation column.

A portion of the first lower part fraction of the second distillation column may be reheated and then refluxed.

All of the upper part fraction of the first distillation column may be fed to the first heat exchanger, and a separate condenser may not be provided in the upper part of the first distillation column.

The heavy raffinate-3 recovered from the lower part of the first distillation column may be reheated, used to preheat the raffinate-2 fed to the first distillation column through a second heat exchanger, and then recovered.

A portion of the heavy raffinate-3 that is reheated after being recovered from the lower part of the first distillation column may be refluxed.

According to the present invention, 1-butene having a purity of 99.0% or more is capable of being recovered at a yield of 80% or more while maximizing heat quantity recovered in a heat exchanger in a process of refining the raffinate-2 stream to reduce energy by 30% or more.

DETAILED DESCRIPTION

Hereinafter, a method according to the present invention is described with reference to FIG. 2. However, FIG. 2 is only an example, and thus it should not be construed as limiting the protection scope of the present invention which is obvious from the claims and throughout the specification.

The present invention relates to a method for economically separating and refining 1-butene with a high purity and a high yield from a raffinate-2 stream discharged from a separation process of a C4 mixture.

In the method according to the invention, raffinate-2 may be all commercially available C4 hydrocarbon mixtures having 1-butene, n-butane, and isobutene. Suitable isobutene-based C4 streams, may be, for example, those obtained in a post-treatment of the stream, such as, those obtained by a refiner, a cracker (e.g. a steam cracker, a cat cracker), Fischer-Tropsch synthesis, dehydrogenation of butane, skeleton isomerization of linear butene, and metathesis of olefins.

Figure 1:
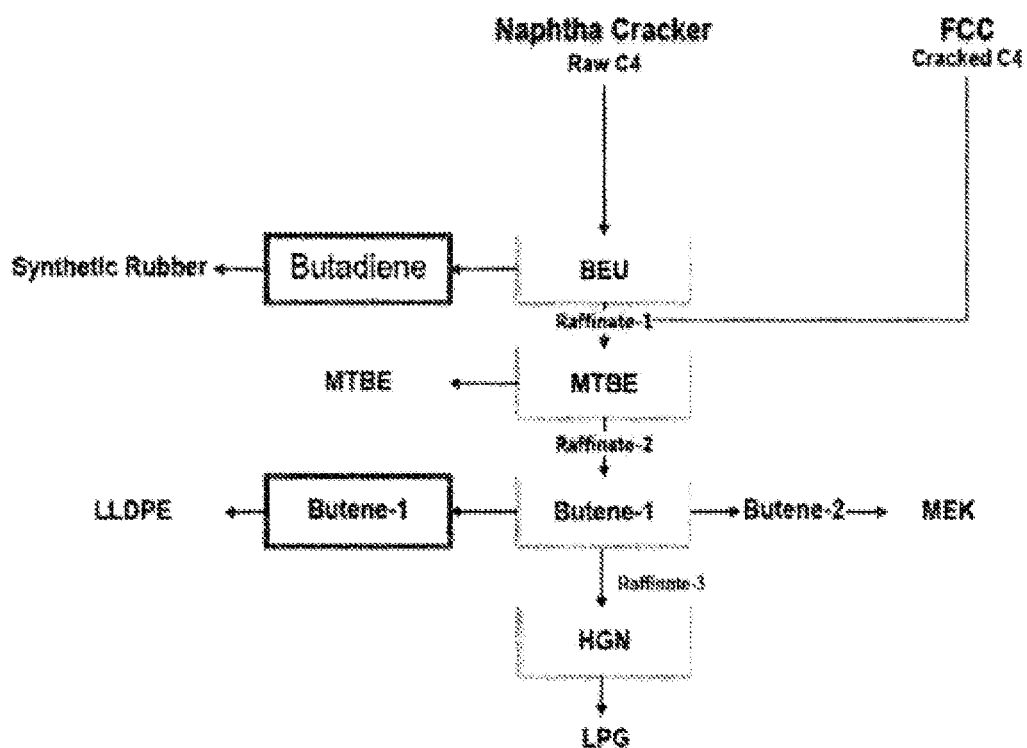
FIG. 1 is a flow chart for explaining a separation step of a C4 mixture according to a conventional separation method.
Figure 2:
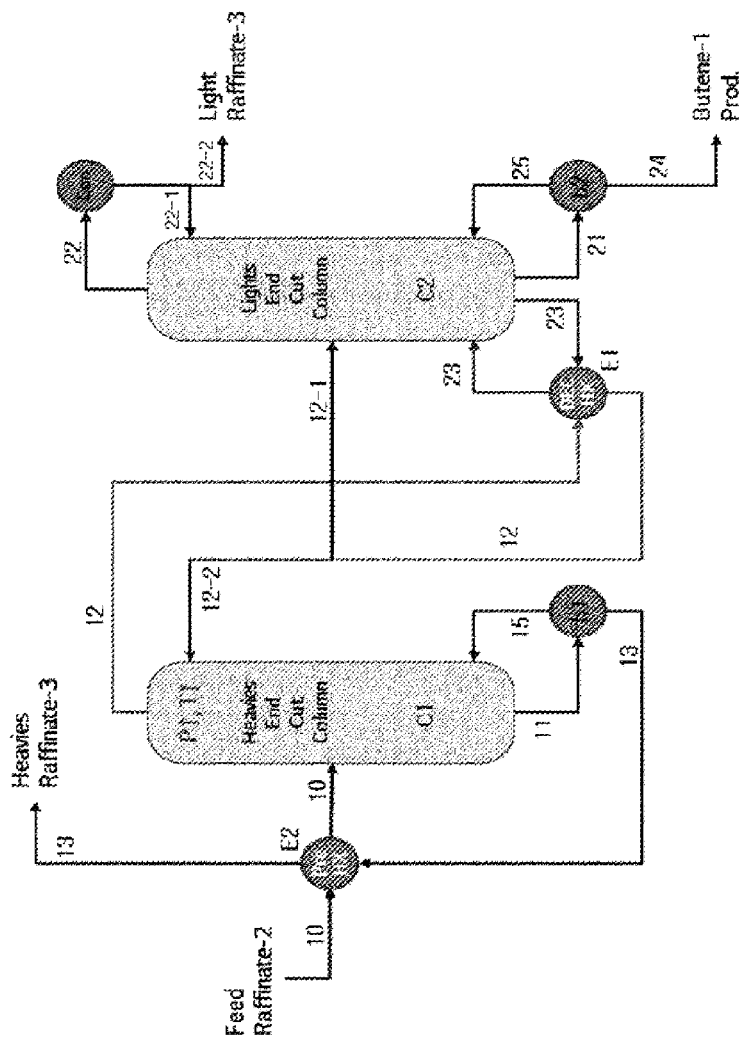
FIG. 2 schematically illustrates a process according to an embodiment of the present invention.

FIG. 2 illustrates a method according to an exemplary embodiment of the present invention.

The method of refining raffinate-2 according to the present invention includes:

feeding a raffinate-2 10 containing n-butane, isobutane, and 1-butene to a first distillation column C1 to obtain heavy raffinate-3 13 containing n-butane from a lower part of the first distillation column C1 and to recover an upper part fraction 12 containing 1-butene from an upper part of the first distillation column; and feeding the upper part fraction 12 containing 1-butene to a second distillation column C2 to recover a first lower part fraction 21 rich in 1-butene from a lower part of the second distillation column C2 and to recover light raffinate-3 22 containing isobutane from an upper part of the second distillation column, wherein heat of the upper part fraction 12 recovered from the upper part of the first distillation column C1 is fed to the lower part of the second distillation column C2 through a first heat exchanger E1.

Here, the raffinate-2 10 fed to the first distillation column C1 preferably contains isobutene and 1-butene at a weight ratio (isobutene/1-butene) of 0.006 or less. This is because 1-butene is not easily separated in a refinement process since 1-butene has almost the same boiling point as isobutene (the boiling point of isobutene is −6.9□ and the boiling point of 1-butene is −6.24□) and it was found that when the ratio of isobutene/1-butene in a feed is higher than 0.0006, it is difficult to design the refinement process, and in severe cases, there is a problem in that it is not possible to manufacture products.

Further, an operating pressure of the second distillation column C2 is preferably 4.7 kgf/cm$^2$ or more, and an operating pressure of the first distillation column is preferably higher than an operating pressure of the second distillation column by 3.5 kgf/cm$^2$ or more. This is because it was found that a condensation temperature of the first distillation column is advantageous for double-effect distillation (DEC) which allows to have pressure sufficient to heat the second distillation column. The preferred range thereof is 3.5 to 5.5 kgf/cm$^2$, or 3.5 to 5.0 kgf/cm$^2$, or 4.0 to 5.5 kgf/cm$^2$ or 4.0 to 5.0 kgf/cm$^2$.

The upper part fraction 12 of the first distillation column C1 may be fed with heat to the second lower part fraction 23 recovered from the lower part of the second distillation column C2 through the first heat exchanger E1, a portion 12-1 of the upper part fraction of the first distillation column may be fed with a feed stream to the second distillation column C2, and the remainder 12-2 may be refluxed to the upper part of the first distillation column C1.

Further, the second lower part fraction 23 of the second distillation column C2 that is fed with heat through the first heat exchanger E1 is refluxed to the second distillation column C2.

Further, a portion 25 of the first lower part fraction 21 of the second distillation column C2 may be reheated and then refluxed to the second distillation column C2.

It is advantageous to divide the lower part fraction of the second distillation column C2 into the first lower part fraction 21 and the second lower part fraction 23 and inject each divided fraction into the heat exchanger since it is usable when all of the heat quantities required for start-up for an initial process and the second distillation column in a reheater b2 are not capable of being fed.

According to an embodiment, all of the upper part fraction 12 of the first distillation column C1 may be fed to the first heat exchanger E1, and a separate condenser may not be provided in the upper part of the first distillation column C1. In other words, the condenser may be omitted by double-effect distillation (DEC) using the first heat exchanger.

The heavy raffinate-3 11 recovered from the lower part of the first distillation column C1 may be reheated, used to preheat the raffinate-2 10 fed to the first distillation column C1 through a second heat exchanger E2, and then recovered.

Here, a portion 15 of the heavy raffinate-3 that is reheated after being recovered from the lower part of the first distillation column C1 may be refluxed.

The method according to the present invention has recovered heat quantity of 6 Gcal/hr or more, thus resulting in very good energy saving effect.

MODE FOR INVENTION

Hereinafter, Examples of the present invention are described.

Example 1

Refinement was performed using raffinate-2 having properties described in Table 1 below and employing the process illustrated in FIG. 2, except that preheating (E2) of raffinate-2 was not performed.

TABLE 1

| Component | Mass Frac. |
| --- | --- |
| C3's | 0.48% |
| C4 paraffin | 29.18% |
| Butene-1 | 43.73% |
| Isobutene | 0.25% |
| C4 olefin | 25.94% |
| C5's | 0.42% |
| Sum | 100.00% |

Example 2

Refinement of raffinate-2 was performed in the same manner as in Example 1, except that preheating (E2) of raffinate-2 was performed as illustrated in FIG. 2.

Example 3

Refinement of raffinate-2 was performed in the same manner as in Example 2, except that a difference in operating pressure between the heavy end elimination column C1 and the light end elimination column C2 was 5.5 kgf/cm².

Comparative Example 1

Figure 3:
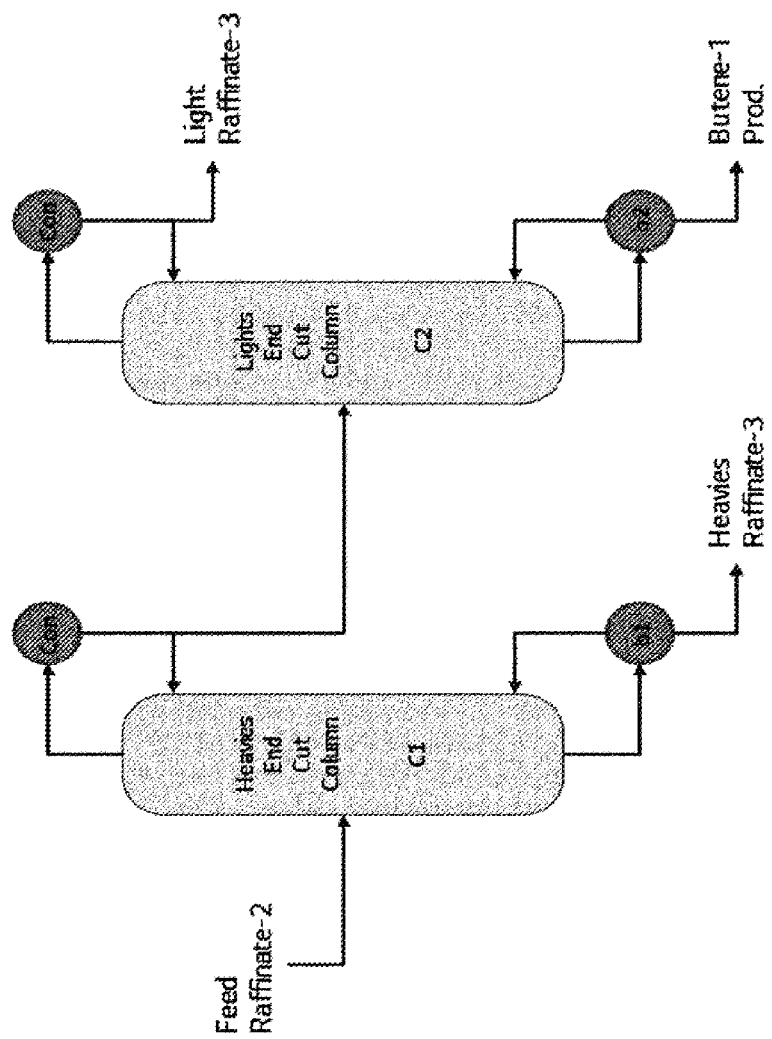
FIG. 3 schematically illustrates a process according to Comparative Example.

The refinement process was performed by using the same raffinate-2 as in Example 1, but not applying double-effect distillation as shown in FIG. 3.

Comparative Example 2

The refinement process was performed in the same manner as in Example 1, except that a ratio of isobutene/1-butene in raffinate-2 was 1% and a difference in operating pressure between the heavy end elimination column C1 and the light end elimination column C2 was 1.1 kgf/cm².

Comparative Example 3

The refinement process was performed in the same manner as in Comparative Example 2, except that a ratio of isobutene/1-butene in raffinate-2 was 0.6% and the operating pressure of the light end elimination column C2 was reduced to 4 kgf/cm².

Comparative Example 4

The refinement process was performed in the same manner as in Comparative Example 2, except that a ratio of isobutene/1-butene in raffinate-2 was 0.6% and a difference in operating pressure between the heavy end elimination column C1 and the light end elimination column C2 was 2.1 kgf/cm².

Table 2 shows comparison results of specific operating conditions and energy recovery rates of Examples 1 to 3 and Comparative Examples 1 to 4.

TABLE 2

| | | Comparative Example 1 | Comparative Example 2 | Comparative Example 3 | Comparative Example 4 | Example 1 | Example 2 | Example 3 |
|---|---|---|---|---|---|---|---|---|
| Feed Condition | Iso-butene/Butene-1 (%) | 0.6 | 1.0 | 0.6 | 0.6 | 0.6 | 0.6 | 0.6 |
| Heavy End Cut Column | Upper Part Pressure (kgf/cm²) | 5.7 | 5.7 | 5.7 | 8.7 | 10.1 | 10.1 | 12.1 |
| | Upper Part Temperature (□) | 51.8 | 51.8 | 51.8 | 67.1 | 73.1 | 73.1 | 80.8 |
| | Feed Temperature (□) | 40.0 | 40.0 | 40.0 | 40.0 | 40.0 | 60.7 | 40.0 |
| | Cond. Q (Gcal/hr) | 5.27 | 5.27 | 5.27 | 6.07 | 6.51 | 6.55 | 7.25 |
| | Reb. Q (Gcal/hr) | 5.40 | 5.40 | 5.40 | 6.30 | 6.78 | 6.69 | 7.58 |
| Light End Cut Column | Upper Part Pressure (kgf/cm²) | 6.6 | 6.6 | 4.0 | 6.6 | 6.6 | 6.6 | 6.6 |
| | Upper Part Temperature (□) | 51.3 | 51.3 | 35.3 | 51.3 | 51.3 | 51.3 | 51.3 |
| | Lower Part Temperature (□) | 61.9 | 61.9 | 46.8 | 61.9 | 61.9 | 61.9 | 61.9 |
| | Product Purity (%) | Spec. in | Spec. Out | Spec. in | Spec. in | Spec. in | Spec. in | Spec. in |
| | Cond. Q (Gcal/hr) | 5.92 | 5.92 | 3.84 | 6.40 | 6.72 | 6.71 | 7.52 |
| | Reb. Q (Gcal/hr) | 5.94 | 5.94 | 3.81 | 6.37 | 6.68 | 6.67 | 7.45 |
| Energy Comparison | Process-recovered Heat (Gcal/hr) | 0.00 | 0.00 | 0.00 | 0.00 | 6.51 | 6.55 | 7.25 |
| | Heat Used for CW (Gcal/hr) | 11.21 | 11.21 | 5.27 | 12.44 | 6.72 | 6.71 | 7.52 |
| | Heat Used for Refrigerant (Gcal/hr) | 0.00 | 0.00 | 3.84 | 0.00 | 0.00 | 0.00 | 0.00 |
| | Total Q (Gcal/hr) | 11.34 | 11.34 | 9.21 | 12.67 | 6.95 | 6.81 | 7.78 |
| | Saving Rate (%) | — | 0.00 | 18.78 | −11.73 | 38.71 | 39.95 | 31.39 |

It could be appreciated from the above-described results that when the weight ratio of isobutene/1-butene in the raffinate-2 to be fed was more than 0.006 (0.6%), it was not possible to satisfy the product specification (99.9% or more) (Comparative Example 2), and when the operating pressure of the light end elimination column (C2) was reduced, thus resulting in an increase of the refrigerant cost and an increase in the energy cost (Comparative Example 3).

In addition, it could be appreciated that when the difference in pressure of the upper part between the heavy end elimination column C1 and the light end elimination column C2 was less than 3.5 kgf/cm$^2$, it was not possible to achieve heat exchange according to double-effect distillation (Comparative Example 4).

On the other hand, it could be appreciated that in Examples 1 to 3 that the difference in pressure of the upper part between the heavy end elimination column C1 and the light end elimination column C2 was 3.5 kgf/cm$^2$ or more, and thus the heat exchange was achieved, and 6 Gcal/hr of heat could be recovered, thereby obtaining an energy saving rate of 30% or more. In addition, it could be appreciated that when the pressure difference was 5.5 kgf/cm$^2$, the energy saving rate was slightly reduced, and thus the optimum pressure difference was in the range of 3.5 to 5.5 kgf/cm$^2$.

Although the present invention has been described with reference to preferred embodiments thereof, the scope of the present invention is not limited thereto, and specific portions of the contents of the present invention have been described in detail. Thus, it will be apparent to those skilled in the art that these specific descriptions are merely preferred embodiments and that the scope of the invention is not limited thereto. Therefore, the substantial scope of the present invention is defined by the accompanying claims and equivalents thereof.

The invention claimed is:

1. A method of refining raffinate-2 comprising:
    feeding a raffinate-2 containing n-butane, isobutane, and 1-butene to a first distillation column;
    obtaining heavy raffinate-3 containing n-butane from a lower part of the first distillation column;
    recovering an upper part fraction containing 1-butene from an upper part of the first distillation column;
    feeding the upper part fraction containing 1-butene to a second distillation column; and
    recovering a first lower part fraction rich in 1-butene recovered from a lower part of the second distillation column and a light raffinate-3 containing isobutane from an upper part of the second distillation column,
    wherein heat of the upper part fraction recovered from the upper part of the first distillation column is fed to a second lower part fraction recovered from the lower part of the second distillation column through a first heat exchanger,
    wherein the upper part fraction of the first distillation column is fed to the first heat exchanger to supply heat from the upper part of the first distillation column to the second lower part fraction through the first heat exchanger, a portion of the upper part fraction of the first distillation column passed through the first heat exchanger is fed as a middle feed stream to the second distillation column, and a remaining portion of the upper part fraction of the first distillation column passed through the first heat exchanger is refluxed as an upper feed stream to the upper part of the first distillation column,
    wherein a position of the middle feed stream is lower than a position of the upper feed stream,
    wherein an upper part pressure of the second distillation column is 4.7 kgf/cm$^2$ or more, and
    wherein an upper part pressure of the first distillation column is higher than the upper part pressure of the second distillation column by 3.5 kgf/cm$^2$ to 5.5 kgf/cm$^2$.

2. The method of claim 1, wherein the raffinate-2 fed to the first distillation column contains isobutene and 1-butene at a weight ratio (isobutene/1-butene) of 0.006 or less.

3. The method of claim 1, wherein the second lower part fraction recovered from the lower part of the second distillation column is refluxed to the second distillation column.

4. The method of claim 1, wherein a portion of the first lower part fraction of the second distillation column is reheated and then refluxed.

5. The method of claim 1, wherein all of the upper part fraction of the first distillation column is fed to the first heat exchanger, and a separate condenser is not provided in the upper part of the first distillation column.

6. The method of claim 1, wherein the heavy raffinate-3 recovered from the lower part of the first distillation column is reheated, and is recovered after being used to preheat the raffinate-2 fed to the first distillation column through a second heat exchanger.

7. The method of claim 6, wherein a portion of the heavy raffinate-3 that is reheated after being recovered from the lower part of the first distillation column is refluxed.

\* \* \* \* \*